(12) United States Patent
Jensen et al.

(10) Patent No.: US 11,419,791 B2
(45) Date of Patent: Aug. 23, 2022

(54) FLEXIBLE CONTAINER SYSTEMS AND NOZZLES, AND RELATED METHODS

(71) Applicant: Fresenius Medical Care Holdings, Inc., Waltham, MA (US)

(72) Inventors: Lynn E. Jensen, Syracuse, UT (US); DeLoy Lindley, North Ogden, UT (US); Natalie Rebacz, Bartlesville, OK (US); Mary Hoover, Shawnee, OK (US); Troy Dayton, Syracuse, UT (US); Michael P. Smith, Ogden, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 750 days.

(21) Appl. No.: 16/028,157

(22) Filed: Jul. 5, 2018

(65) Prior Publication Data
US 2020/0009018 A1    Jan. 9, 2020

(51) Int. Cl.
*A61J 1/20* (2006.01)
*A61M 1/16* (2006.01)
(Continued)

(52) U.S. Cl.
CPC ............. *A61J 1/2093* (2013.01); *A61J 1/10* (2013.01); *A61M 1/167* (2014.02);
(Continued)

(58) Field of Classification Search
CPC ........................... A61J 1/1481; A61M 1/1668
See application file for complete search history.

(56) References Cited

U.S. PATENT DOCUMENTS

| | | |
|---|---|---|
| 4,526,572 A | 7/1985 | Donnan et al. |
| 5,366,162 A | 11/1994 | Strizki |

(Continued)

FOREIGN PATENT DOCUMENTS

| | | |
|---|---|---|
| CN | 201058192 Y | 5/2008 |
| EP | 0624085 B1 | 10/1997 |

(Continued)

OTHER PUBLICATIONS

International Search Report for International Application No. PCT/US19/36833, dated Sep. 27, 2019, 5 pages.

(Continued)

*Primary Examiner* — Elizabeth Insler
(74) *Attorney, Agent, or Firm* — TraskBritt

(57) ABSTRACT

A container system includes at least one flexible wall defining a compartment containing a dissolvable solid or concentrate, a support adjacent a first end of the at least one flexible wall, and a nozzle assembly coupled to a second end of the at least one flexible wall. The second end of the wall is distal from the first end. The nozzle assembly comprises a hollow body defining a longitudinal axis. The hollow body further defines a plurality of orifices through a wall thereof. Each orifice is able to form a fluid connection between an interior volume within the hollow body and the compartment. Each orifice is configured to deliver liquid from the interior volume to the compartment in a direction having an angle of between 5° and 85° from a direction of the longitudinal axis. Related nozzles and methods are also disclosed.

11 Claims, 6 Drawing Sheets

(51) Int. Cl.
*A61J 1/10* (2006.01)
*A61M 1/28* (2006.01)

(52) U.S. Cl.
CPC .......... *A61M 1/1666* (2014.02); *A61J 1/2024* (2015.05); *A61M 1/287* (2013.01)

(56) References Cited

U.S. PATENT DOCUMENTS

| | | |
|---|---|---|
| 5,372,312 A | 12/1994 | Vidusek |
| 6,007,478 A | 12/1999 | Siess et al. |
| 6,071,005 A * | 6/2000 | Ekambaram .......... B01F 5/0068 366/165.1 |
| 7,169,138 B2 | 1/2007 | Becker et al. |
| 8,328,784 B2 | 12/2012 | Jensen et al. |
| 9,095,499 B2 | 8/2015 | Kugelmann et al. |
| 9,138,380 B2 | 9/2015 | Jansson et al. |
| 9,198,830 B2 | 12/2015 | Kugelmann et al. |
| 9,539,175 B2 * | 1/2017 | Carlsson ............... A61J 1/2093 |
| 9,585,810 B2 | 3/2017 | Jensen et al. |
| 9,855,378 B2 | 1/2018 | Brandl et al. |
| 2002/0189684 A1 | 12/2002 | Williamson et al. |
| 2007/0029001 A1 | 2/2007 | Trouilly et al. |
| 2014/0026761 A1 | 1/2014 | Bartoli et al. |
| 2015/0029817 A1 * | 1/2015 | Orszullok ........... B01F 15/0085 366/336 |
| 2016/0213832 A1 | 7/2016 | Eyrard et al. |
| 2016/0326946 A1 | 11/2016 | Willi |
| 2016/0375221 A1 | 12/2016 | Panotopoulos et al. |
| 2017/0319769 A1 | 11/2017 | Wieslander et al. |

FOREIGN PATENT DOCUMENTS

| | | |
|---|---|---|
| EP | 1101080 B1 | 5/2008 |
| EP | 2537541 A1 | 12/2012 |
| EP | 2695633 A1 | 2/2014 |
| WO | 2007/068032 A1 | 6/2007 |

OTHER PUBLICATIONS

International Written Opinion for International Application No. PCT/US19/36833, dated Sep. 27, 2019, 8 pages.

European Partial Supplemental Partial Search Report and Opinion for European Application No. 19831040.1, dated Mar. 17, 2022, 17 pages.

* cited by examiner

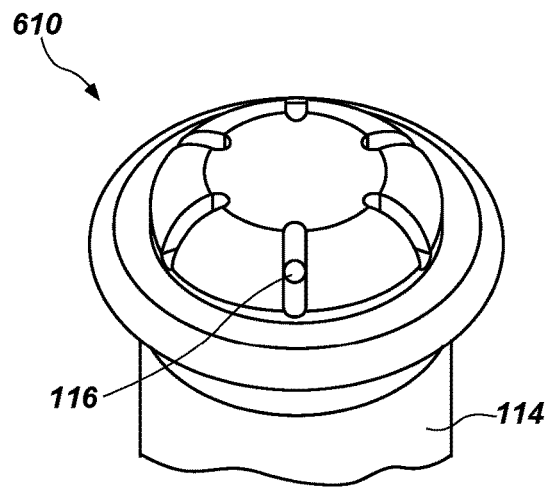
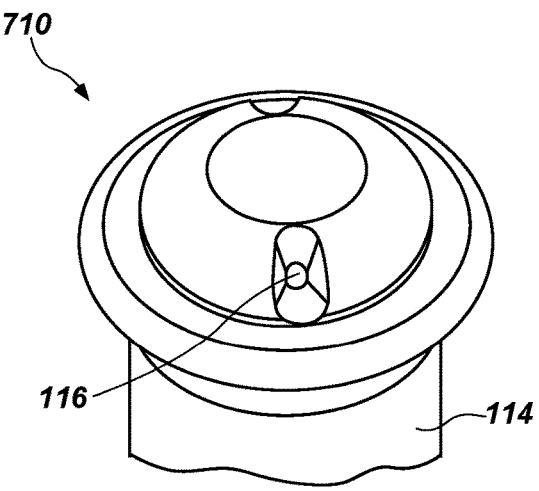
FIG. 6     FIG. 7
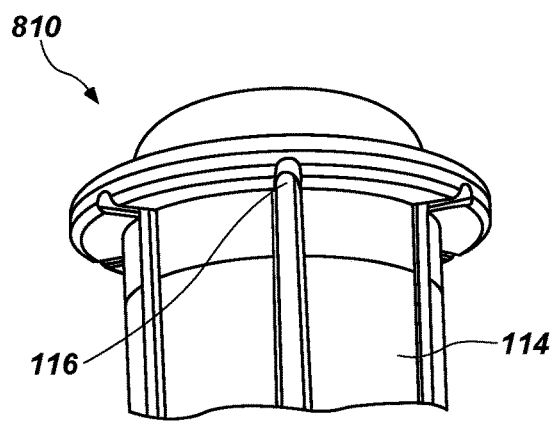
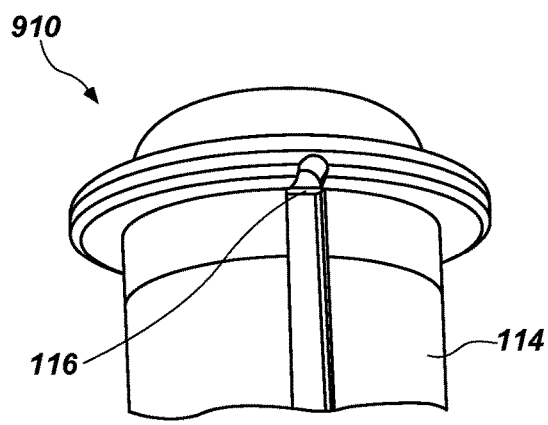
FIG. 8     FIG. 9

FLEXIBLE CONTAINER SYSTEMS AND NOZZLES, AND RELATED METHODS

FIELD

Embodiments of the application relate generally to container systems that may be used, for example, in preparing and delivering solutions to patients, such as solutions for dialysis.

BACKGROUND

Dialysis is commonly used to replace kidney function lost by kidney disease. Most importantly, dialysis is designed to remove waste toxins and excess water from the blood. In one type of dialysis—hemodialysis (HD)—toxins are filtered from a patient's blood through a dialyzer separated by a semi-permeable membrane from a large volume of external dialysis solution. The waste and toxins dialyze out of the blood through the membrane into the dialysis solution, which is then discarded.

Peritoneal dialysis (PD) is an alternative method that makes use of a natural, semi-permeable membrane surrounding the walls of the patient's abdomen or peritoneal cavity (i.e., the peritoneum). During a PD procedure, a solution is introduced into the patient's abdomen, where it remains for up to several hours, removing toxins via diffusion across the membrane. This solution is then drained from the body along with the toxins dissolved therein.

Dialysis solutions generally include water and glucose, electrolytes (e.g., sodium, calcium, potassium, chlorine, magnesium, etc.), acids (e.g., citric acid, acetic acid, etc.) and/or bases (e.g., bicarbonate). These solutions may be premixed or may be shipped as concentrates or powders to be mixed to a final concentration at the point of use. Premixed solutions are more expensive to ship and store. Shipping and storing concentrates or powders is cheaper, but increases costs for mixing on-site at the time of use (e.g., in the form of additional steps for a medical practitioner).

Mixing requires addition of purified water and agitation over a period of time to ensure a solution of uniform concentration. Conventional dialysis processes may require the use of one supply line to add liquid to the solution container and a second line to remove liquid from the solution container, which lines complicate manufacture and use, and increases costs.

BRIEF SUMMARY

In some embodiments, a container system includes at least one flexible wall defining a compartment containing a dissolvable solid or concentrate, a support adjacent a first end of the at least one flexible wall, and a nozzle assembly coupled to a second end of the at least one flexible wall. The second end of the wall is distal from the first end. The nozzle assembly comprises a hollow body defining a longitudinal axis. The hollow body further defines a plurality of orifices through a wall thereof. Each orifice is able to form a fluid connection between an interior volume within the hollow body and the compartment. Each orifice is configured to deliver liquid from the interior volume to the compartment in a direction having an angle of between 5° and 85° from a direction of the longitudinal axis.

In some embodiments, a nozzle assembly includes a hollow body having a generally cylindrical exterior surface and defining a longitudinal axis, and a port configured to couple to a catheter. The hollow body defines a plurality of orifices therethrough. Each orifice is able to form a fluid connection between an interior volume within the hollow body and an exterior volume outside the nozzle assembly. Each orifice is configured to deliver liquid received from the port to the exterior volume in a direction forming an angle of between 5° and 85° with respect to a direction of the longitudinal axis of the hollow body.

A method for delivering a liquid includes providing a plurality of streams of a liquid through a nozzle assembly into a compartment containing a dissolvable solid or concentrate, mixing the dissolvable solid or concentrate with the liquid to form a solution; and withdrawing the solution after mixing from the compartment through the nozzle assembly. The compartment is defined by at least one flexible wall having a support adjacent a first end of the at least one flexible wall. The nozzle assembly is coupled to a second end of the at least one flexible wall distal from the first end. The nozzle assembly includes a hollow body defining a longitudinal axis. The hollow body defines a plurality of orifices therethrough, each orifice able to form a fluid connection between an interior volume within the hollow body and the compartment. Each orifice is configured to deliver the liquid from the interior volume to the compartment in a direction having an angle of between 5° and 85° from a direction of the longitudinal axis.

The mixing process can be completed relatively quickly, such that the solution may be withdrawn shortly after the streams of liquid are first provided into the compartment. Furthermore, the nozzle design enables the use of a single fluid line to fill the compartment and remove the mixed solution. Thus, the container system may expedite and simplify the process of providing the mixed solution.

BRIEF DESCRIPTION OF THE DRAWINGS

FIG. 6 is a simplified perspective view of a nozzle assembly.

FIG. 7 is a simplified perspective view of another nozzle assembly.

FIG. 8 is a simplified perspective view of another nozzle assembly.

FIG. 9 is a simplified perspective view of another nozzle assembly.

DETAILED DESCRIPTION

The illustrations presented herein are not actual views of any particular container system, but are merely idealized representations that are employed to describe example embodiments of the disclosure. Additionally, elements common between Figures may retain the same numerical designation.

Figure 1:
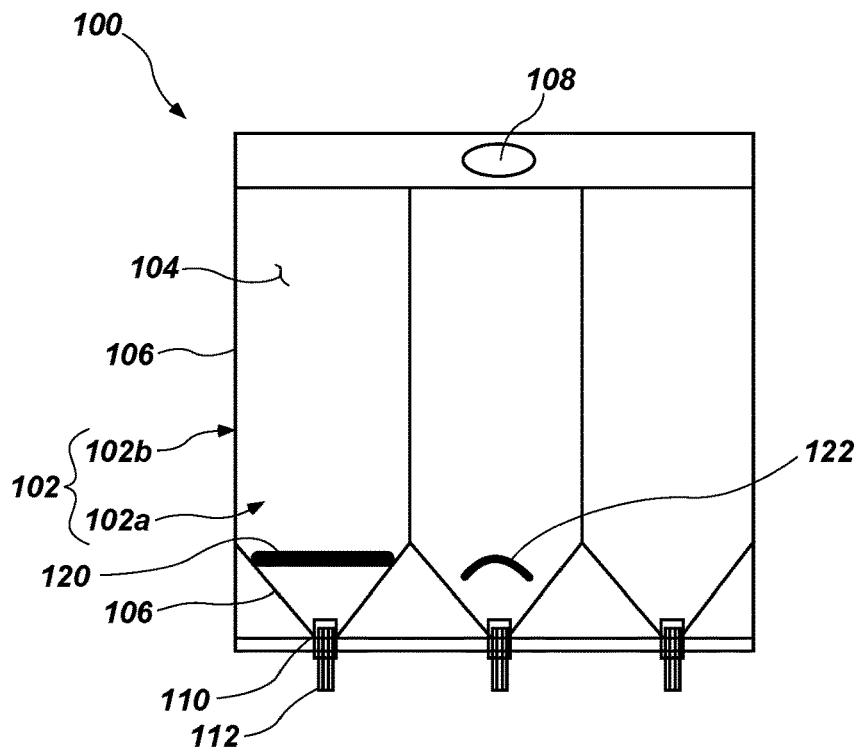
FIG. 1 is a simplified side view illustrating an embodiment of a container system.

FIG. 1 illustrates a container system 100. The illustrated container system 100 is configured to contain liquids used for dialysis, such as electrolytes, bicarbonate, sodium chloride, dextrose, etc.

The container system 100 is illustrated as including at least one flexible wall 102 defining a compartment 104. For example, the at least one flexible wall 102 shown in FIG. 1 includes a front wall 102a and a rear wall 102b, with a seam 106 connecting the front wall 102a to the rear wall 102b. The flexible wall 102 may be polyvinyl chloride (PVC), monomaterial ethylene vinyl acetate (EVAM), polyolefin, polyethylene, polypropylene, polyamides, etc. The flexible wall 102 may be, for example, a single material or layers of different materials.

The container system 100 shown in FIG. 1 includes three separate compartments 104, but any number of compartments 104 may be defined by the flexible wall 102. In some embodiments, the compartments 104 may have rigid walls, or a combination of rigid and flexible walls. FIG. 1 is not drawn to scale, and there is no particular limitation on the dimensions or ratio of dimensions of the container system 100.

Figure 2:
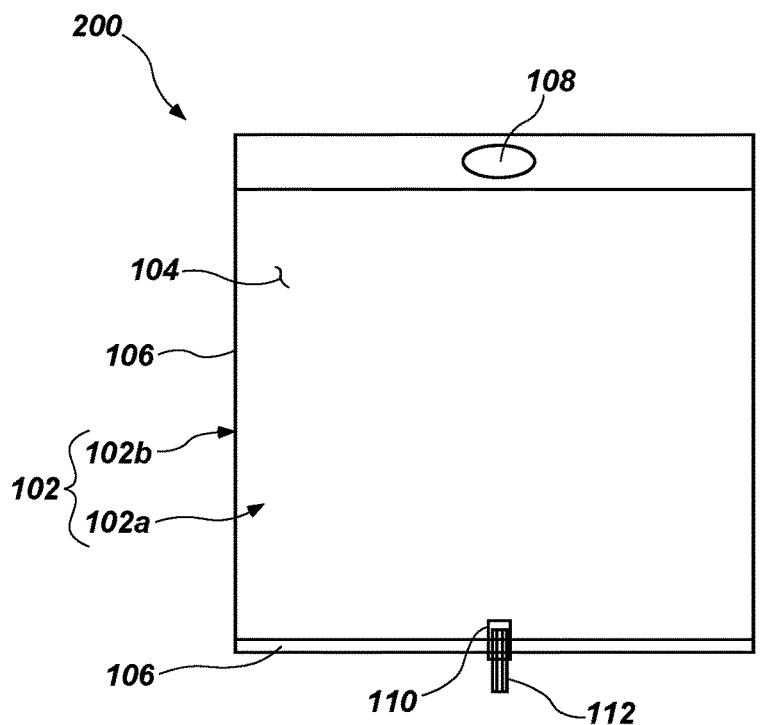
FIG. 2 is a simplified side view illustrating another embodiment of a container system.

FIG. 2 shows an embodiment of a container system 200 that has a single compartment. The seam 106 may be a continuous or nearly continuous seal surrounding the compartment 104. In some embodiments, such a flexible wall 102 may include a single wall (e.g., a generally cylindrical wall). Nonetheless, the flexible wall 102 and the seam 106 may substantially enclose the compartment 104. The seam 106 may be, for example, a melt-bonded portion of the flexible wall 102, an ultrasonically welded portion of the flexible wall 102, an adhesive, etc.

The compartment 104 may contain a dissolvable solid or a concentrate (i.e., a liquid, typically with a compound dissolved therein) that may be used to form a dialyzing solution. For example, the compartment 104 may contain sodium bicarbonate, sodium chloride, dextrose, a buffer, an electrolyte, etc., or any combination thereof.

The container system 100 may include a support 108 to facilitate maintaining the container system 100 in an upright position (FIG. 1). For example, the support 108 may include a hole through the flexible wall 102, a hook, or other structure adapted to attach to a fixed or movable object (e.g., an IV pole). In some embodiments, the support 108 includes a portion of the seam 106, to which a clamp or other device may be attached.

The container system 100 includes a nozzle assembly 110 and a fluid conduit (e.g., a catheter) coupled to a port 112 to provide a fluid connection to the compartment 104. The nozzle assembly 110 may include materials such as polyvinyl chloride (PVC), monomaterial ethylene vinyl acetate (EVAM), polyolefin, polyethylene, polypropylene, polycarbonate, polyamides, etc. The flexible wall 102 may be a single material or layers of different materials. The nozzle assembly 110 may be coupled to an end of the flexible wall 102 at an opposite end of the compartment 104 from the support 108, such that when the container system 100 is hanging from a structure (e.g., an IV pole), the nozzle assembly 110 is at the bottom of the compartment 104. The nozzle assembly 110 may be the only fluid connection to the compartment 104 (or, as pictured in FIG. 1, the only fluid connection to each compartment 104 in a container system 100 having multiple compartments 104).

Figure 3:
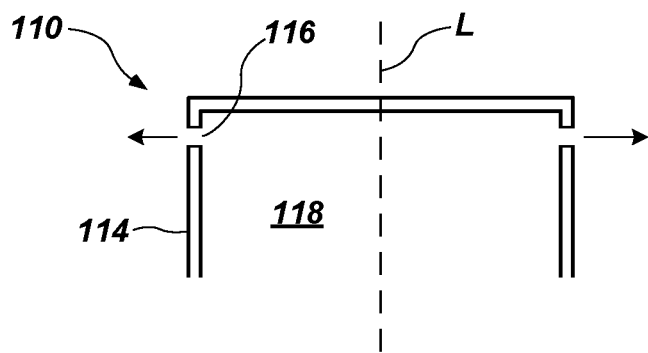
FIG. 3 is a simplified cross-sectional side view of a portion of a nozzle assembly that may be used in a container system.

The nozzle assembly 110 may include a hollow body having a generally cylindrical exterior surface and a plurality of orifices extending through a wall of the hollow body. The port 112 may be integral to the nozzle assembly 110, and may be, for example, a screw connector, a barbed connector, a frangible connector, etc. Each orifice is capable of forming a fluid connection between an interior volume within the hollow body and the compartment 104. FIG. 3 is a simplified cross-sectional side view of a portion of a nozzle assembly 110, such as the nozzle assemblies 110 shown in FIGS. 1 and 2. The nozzle assembly 110 may include a hollow body 114 having a generally cylindrical exterior surface, but may alternatively have a non-cylindrical shape. The hollow body 114 defines a plurality of orifices 116 therethrough. Each orifice 116 is able to form a fluid connection between an interior volume 118 within the hollow body 114 and the compartment 104 (FIGS. 1 and 2).

As shown in FIG. 3, at least some of the orifices 116 may be oriented such that liquid flowing through the orifices 116 leaves the nozzle assembly 110 in a direction substantially perpendicular to a longitudinal axis L of the nozzle assembly 110.

Figure 4:
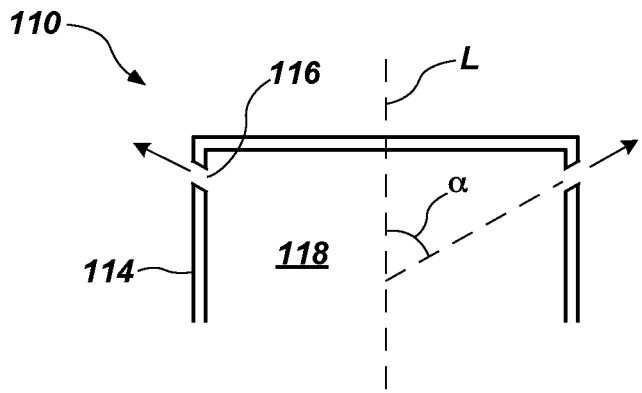
FIG. 4 is a simplified cross-sectional side view of a portion of a nozzle assembly that may be used in a container system.

FIG. 4 is a simplified cross-sectional side view of a portion of a nozzle assembly 110, such as the nozzle assemblies 110 shown in FIGS. 1 and 2. The nozzle assembly 110 of FIG. 4 may be the same nozzle assembly 110 shown in FIG. 3 (i.e., as viewed along a different plane) or may be a different nozzle assembly 110. As shown in FIG. 4, at least some of the orifices 116 may be oriented such that liquid flowing through the orifices 116 leaves the nozzle assembly 110 at an acute angle α with respect to the longitudinal axis L of the nozzle assembly 110. The angle α may be, for example, between 5° and 85°, such as at least 10°, at least 30°, at least 45°, or even at least 60°.

Figure 5:
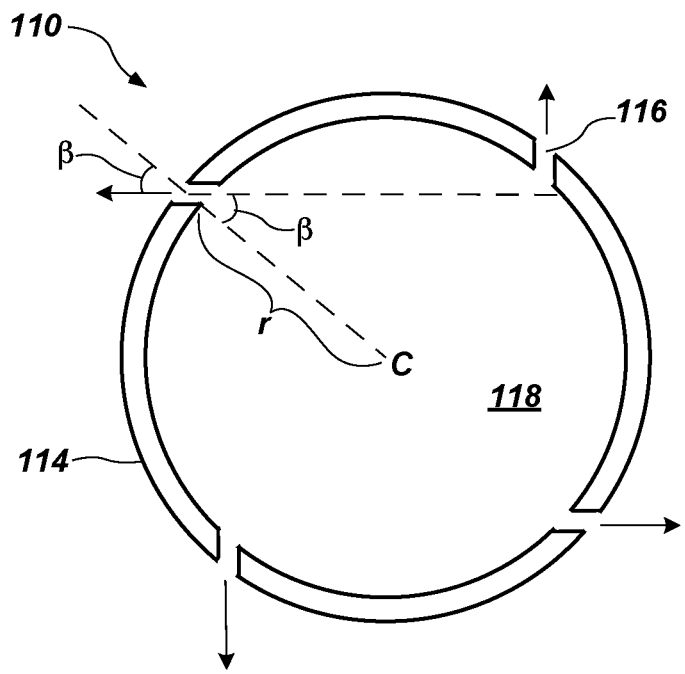
FIG. 5 is a simplified cross-sectional top view of a portion of a nozzle assembly that may be used in a container system.

FIG. 5 is a simplified cross-sectional top view of a portion of a nozzle assembly 110, such as the nozzle assemblies 110 shown in FIGS. 1 and 2. In some embodiments, and as shown in FIG. 5, at least some of the orifices 116 in the nozzle assembly 110 may be oriented such that fluid leaving the orifices 116 travels in a direction at an angle β with respect to a direction normal to an exterior surface of the nozzle assembly 110. If the exterior of the nozzle assembly 110 is circular, the angle β is the same as the angle β between the direction of flow from the orifice 116 and the radius r passing through the orifice 116 and the center C of the nozzle assembly 110. The angle β may be at least 5°, at least 10°, at least 30°, at least 45°, or even at least 60°. In some embodiments, the orifices 116 may be oriented such that they form an acute angle α with respect to the longitudinal axis L of the nozzle assembly 110, as well as a nonzero angle β with respect to the radius r. That is, the direction of flow may form a line skew with respect to the longitudinal axis L. Such flow directions may promote the mixing of liquids and optionally solids within the compartment 104 because liquid entering through the nozzle assembly 110 may tend to form a vortex in the compartment 104 as the liquid exits the nozzle assembly 110. Thus, the nozzle assembly 110 as shown in FIGS. 1-5 herein may promote mixing more efficiently than conventional fluid nozzles.

FIGS. 6-9 are simplified perspective views of some nozzle assemblies 610, 710, 810, and 910, such as the nozzle assembly 110 shown in FIGS. 1-5. The nozzle assembly 610 shown in FIG. 6 has six orifices 116 arranged circumferentially around the nozzle assembly 610, but any number of orifices may be present in other embodiments. The nozzle assembly 710 shown in FIG. 7 has two orifices 116 arranged 180° apart. The orifices 116 shown in FIGS. 6 and 7 are each oriented at an angle with respect to the longitudinal axis L (see FIG. 4) of the nozzle assemblies 610 and 710, such that liquid steams leaving the nozzle assemblies 610 and 710 travel generally outward and upward at an angle when the nozzle assemblies 610 and 710 are oriented in an upright position.

The nozzle assembly 810 shown in FIG. 8 has six orifices 116 (three of which are visible) arranged circumferentially around the nozzle assembly 810, but any number of orifices may be present. The nozzle assembly 910 shown in FIG. 9 has two orifices 116 arranged 180° apart (one of which is visible). The orifices 116 shown in FIGS. 8 and 9 are oriented perpendicular to the longitudinal axis L (see FIG. 3) of the nozzle assemblies 810 and 810, such that liquid steams leaving the nozzle assemblies 810 and 910 travel generally horizontally when the nozzle assemblies 810 and 910 are oriented in an upright position.

Figure 10:
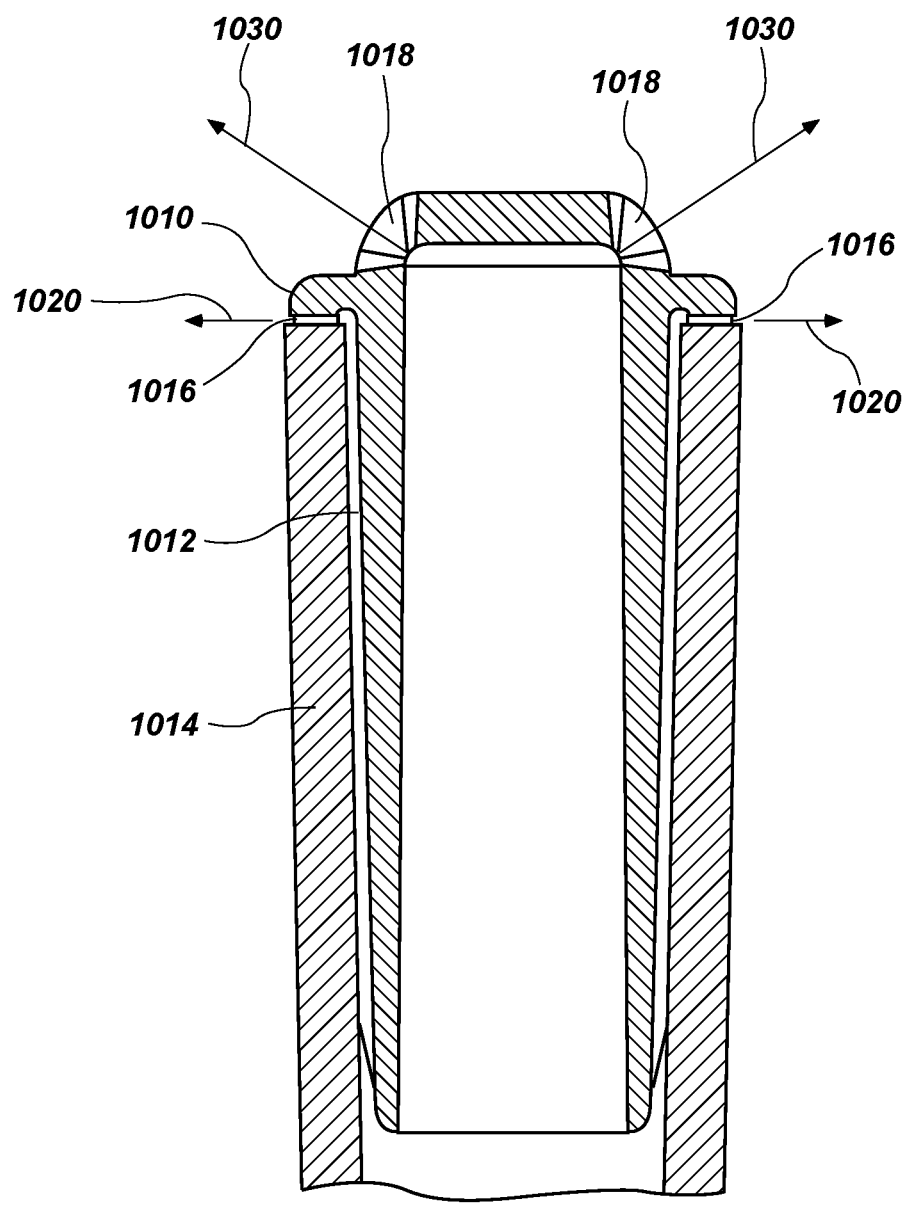
FIG. 10 is a simplified cross-sectional view of another nozzle assembly.

FIG. 10 is a simplified cross-sectional view of another nozzle assembly 1010. The nozzle assembly 1010 may be disposed within a flange 1014. The flange 1014 and the nozzle assembly 1010 may together define flow channels 1012 leading to orifices 1016 (e.g., orifices oriented similar to the orifices 116 shown in FIG. 9). Fluid may leave the orifices 1016, for example, in a lateral direction 1020. Fluid may also pass through the nozzle assembly 1010 out upper orifices 1018 (e.g., orifices oriented similar to the orifices 116 shown in FIG. 7) in an angled direction 1030. The direction 1030 may be, for example, from about 5° to about 85° (e.g., at least 10°) with respect to an angle normal to the surface of the nozzle assembly 1010. Thus, the nozzle assembly 1010 may include features of the nozzle assembly 710 shown in FIG. 7 and the nozzle assembly 910 shown in FIG. 9.

Returning again to FIGS. 1 and 2, a fluid conduit coupled to the port 112 may be configured to provide a liquid (e.g., water) to the compartment 104 through the nozzle assembly 110. The liquid may be mixed with a dissolvable solid or concentrate in the compartment 104 to form a solution. The nozzle assembly 110 is configured to receive the solution from the compartment 104 and deliver the solution to the fluid conduit via the port 112, such that the solution may be used for a biological process (e.g., transferred to a patient). In some embodiments, the nozzle assembly 110 extends into the compartment a distance between about 1 mm and about 10 mm In some embodiments, and as shown in FIG. 1, the seam 106 adjacent the nozzle assembly 110 may form the interior of the container system 100 into a conical shape. The nozzle assembly 110 may be adjacent the bottom (in the orientation of FIG. 1) of the conical portion of the compartment 104. Thus, when the container system 100 is upright, the solid or concentrate in the compartment 104 may generally rest near the nozzle assembly 110. Thus, the flow of liquid into the compartment 104 may cause movement of the solid or concentrate, which may promote dissolution in the liquid. The orifices 116 (FIG. 4) are configured to deliver liquid from the interior volume 118 of the nozzle assembly 110 to the compartment 104 in a direction substantially parallel to the seam 106 at the bottom of the container system 100.

In some embodiments, and as shown in FIG. 2, the seam 106 adjacent the nozzle assembly 110 form the interior of the container system 200 into a rectangular shape. The nozzle assembly 110 may be adjacent the bottom (in the orientation of FIG. 2) of the compartment 104. Thus, when the container system 200 is upright, the solid or concentrate in the compartment 104 generally rests along the lower seam 106. The orifices 116 (FIG. 3) may be configured to deliver liquid from the interior volume 118 of the nozzle assembly 110 to the compartment 104 in a direction substantially horizontally, parallel to the seam 106 at the bottom of the container system 100.

In some embodiments, and as shown in FIG. 1, the container system 100 can include a frangible seal 120 configured to limit, restrict, or even prevent the transfer of material from the compartment 104 until the frangible seal 120 has been breached. The frangible seal 120 may be, for example, a peel seal. The frangible seal 120 may enable the container system 100 to be shipped and stored with the solid or concentrate inside the compartment 104. In certain embodiments, the container system 100 may include a frangible seal coupled to the port 112, such as described in U.S. Pat. No. 9,585,810, "Systems and methods for delivery of peritoneal dialysis (PD) solutions with integrated inter-chamber diffuser," issued Mar. 7, 2017, the entire disclosure of which is hereby incorporated by reference.

In some embodiments, the container system 100 includes a barrier 122 within the compartment 104 to direct flow from the nozzle assembly 110. The barrier 122 may direct incoming liquid along the lower seam 106 to cause mixing of the solid or concentrate. For example, the barrier 122 may be circular as pictured, have straight edges, or any combination thereof.

In some embodiments, the container system 100 (FIG. 1) is used to prepare and deliver a solution, such as to a patient's body for dialysis. Liquid is provided to the nozzle assembly 110 via the fluid conduit coupled to the port 112. To begin providing the liquid, the frangible seal 120 may first be breached. The liquid may form a plurality of streams and pass through the nozzle assembly 110 into the compartment 104. The streams may mix with the solid(s) or concentrate within the compartment 104 and form a solution having a relatively uniform composition within the compartment 104. The steams may form a rotational flow of liquid within the compartment 104. In some embodiments, the solution within the compartment 104 may optionally be further agitated by other means, such as by manually shaking or otherwise manipulating the container system 100.

The solution within the compartment 104 may be withdrawn from the compartment 104 through the nozzle assembly 110, the port 112, and the fluid conduit. The solution may be withdrawn through the same fluid conduit that was used to provide the liquid to the compartment 104. Thus, an operator (e.g., a health-care provider) may need to connect a catheter or other fluid conduit to the container system 100 at a single point. The direction of fluid flow (i.e., into or out of the compartment 104) may be controlled by one or more valves, pumps, etc. The solution may be withdrawn from the compartment 104 at a variable flow rate. For example, the solution may have an initial flow rate when the solution starts flowing, and may decrease in a stepwise manner after a period of time. For example, there may be multiple step changes in the flow rate. In some embodiments, the flow rate may decrease continuously. In other embodiments, the flow rate may increase over time.

The mixing process may be completed relatively quickly (i.e., the variance in composition of the solution may be within a selected level, such as within 1%, within 0.5%, or even within 0.1%). Verification that the mixing process has been completed may be visual inspection (e.g., observing whether any undissolved solid remains), by conductivity testing, or any other method or combination of methods. In some embodiments, the solution may begin to be withdrawn less than 10 minutes after the steams of liquid are first provided into the compartment 104, less than 5 minutes after the steams of liquid are first provided into the compartment 104, or even less than 2 minutes after the steams of liquid are first provided into the compartment 104. Thus, the container system 100 may expedite and simplify the process of providing the mixed solution, such as to a patient.

Figure 13:
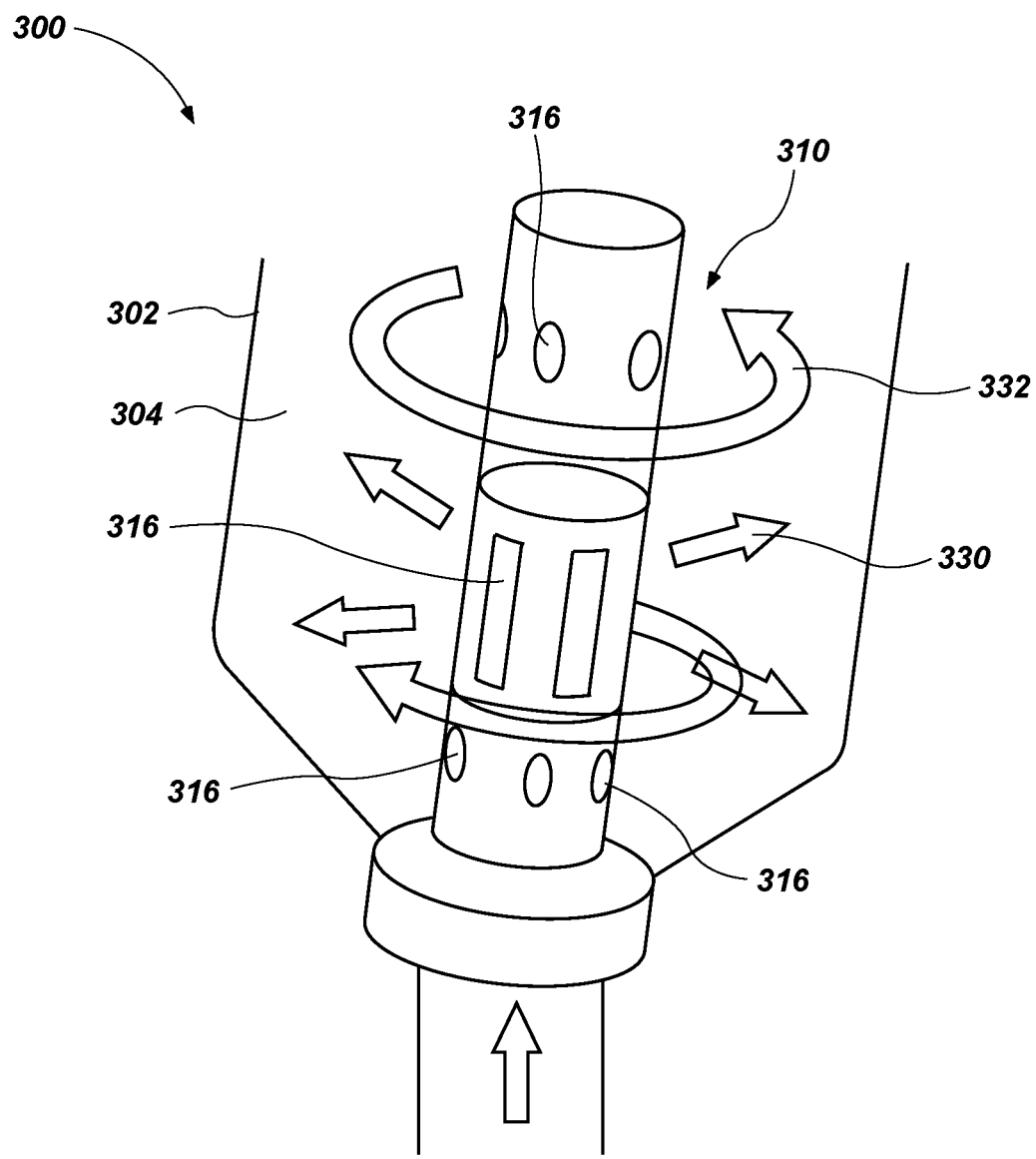
FIG. 13 is a simplified perspective view illustrating an embodiment of another container system.

FIG. 13 illustrates another embodiment of a container system 300, and includes a flexible wall 302 and a nozzle assembly 310. The flexible wall 302 defines a compartment 304 therein. The nozzle assembly 310 has orifices 316 of different sizes, shapes, and orientations. Though FIG. 13 depicts three rows of orifices 316, any number, type, and arrangement of orifices 316 may be present. For example, some orifices 316 are depicted as circular, and some are depicted as rectangular, though other shapes may be use. Flow of liquid into the compartment 104 through the nozzle assembly 310 may be in both an outward direction 330 and a rotational direction 332. In some embodiments, sections of the nozzle assembly 310 may rotate with respect to one another, such that the orifices 316, and therefore streams of the liquid, are oriented to spray in different directions at different times.

EXAMPLES

Example 1

Figure 11:
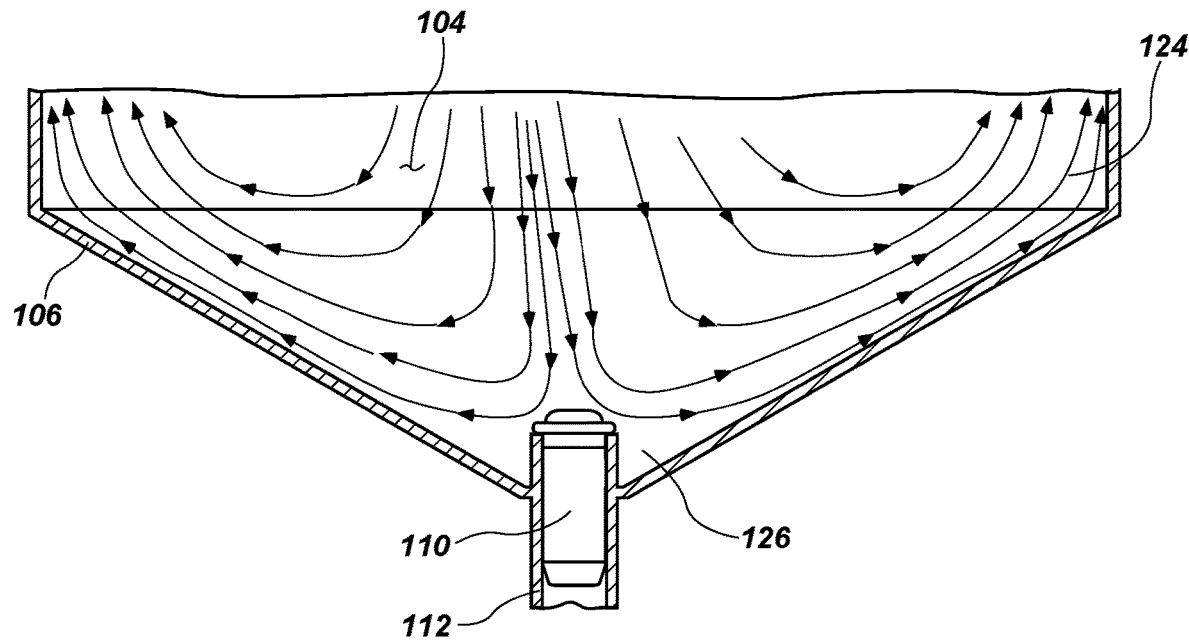
FIG. 11 is a simplified cross-sectional view of a portion of a container system showing streamlines of fluid flow within the container system.

FIG. 11 illustrates theoretical streamlines 124 of fluid flowing into a compartment 104. The compartment 104 has a seam 106 oriented at an acute angle of approximately 30° with respect to horizontal as shown. Two streams of the liquid leaving the nozzle assembly 110 are angled generally parallel to the seam 106, at approximately 30° from horizontal. The streams circulate the liquid within the compartment 104 and mix with the solid or concentrate within the compartment 104. Based on the height of the nozzle assembly 110 and the orientation of the seam 106, a volume 126 may be present in which there is minimal mixing (as indicated by a lack of streamlines 124 in the volume 126).

Example 2

Figure 12:
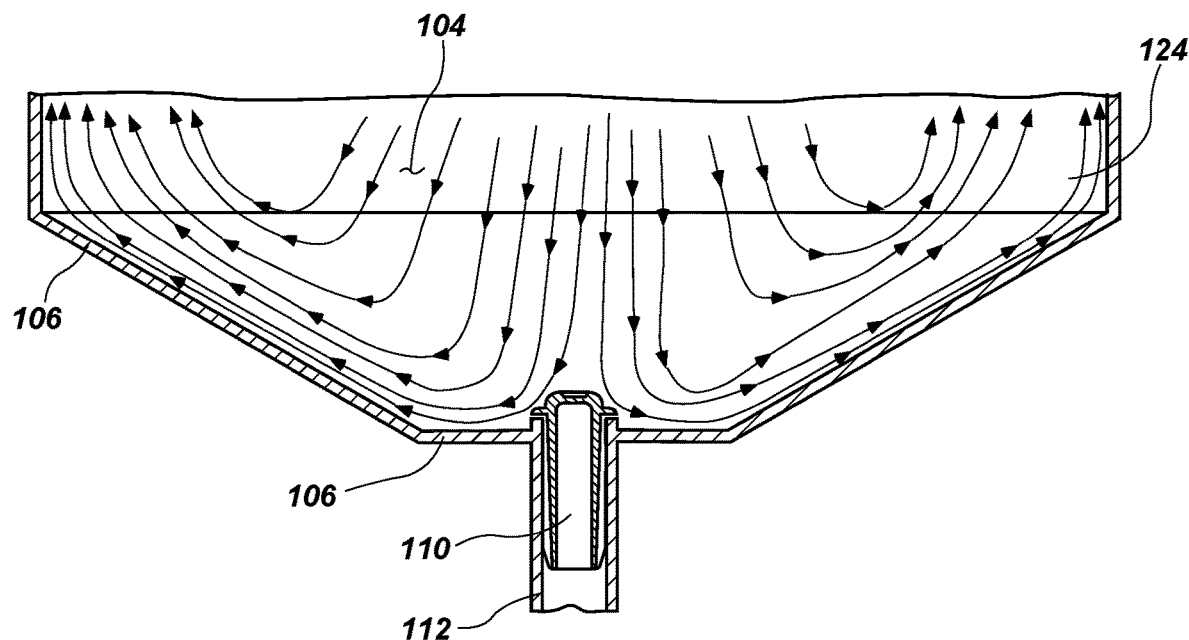
FIG. 12 is a simplified cross-sectional view of a portion of another container system showing streamlines of fluid flow within the container system.

FIG. 12 illustrates theoretical streamlines 124 of fluid flowing into a compartment 104. The compartment 104 has a seam 106 with a portion surrounding the nozzle assembly 110 oriented horizontally. Two streams of liquid leave the nozzle assembly 110 horizontally. The streams circulate the liquid within the compartment 104 and mix with the solid or concentrate within the compartment 104. Based on the height of the nozzle assembly 110 and the orientation of the seam 106, the entire volume or substantially the entire volume of the lower portion of the compartment 104 may be mixed by the streams (as indicated by the distribution of the streamlines 124 even at the lower portions of the compartment 104).

Example 3

Container systems were formed as shown in FIG. 12, having a width of 113 mm, each containing 52.92 g of sodium bicarbonate. Water was added through a nozzle assembly as shown in FIG. 9, with a nominal orifice area of 1.1 mm$^2$, at various flow rates between 350 g/min and 510 g/min, and at temperatures from 17° C. to 42° C. The container systems were filled to contain approximately 1.0 L (one liter) of solution. All the sodium bicarbonate was dissolved by the time 1,000 g of the water had been provided into the container system.

Example 4

Container systems were formed as shown in FIG. 12, having a width of 113 mm, each containing 38.4 g of potassium chloride, 31.5 g of calcium chloride dihydrate, and 6.5 g of magnesium chloride hexahydrate. Water was added through a nozzle assembly as shown in FIG. 9, the nozzle having an effective area of 0.397 mm$^2$, at various flow rates between 400 g/min and 500 g/min, and at temperatures from 15° C. to 39° C. All the solids had dissolved by the time 500 g of the water had been provided into the container system.

Example 5

Container systems were formed as shown in FIG. 12, having a width of 81 mm, each containing 13.0 g of sodium chloride and 10.0 g of dextrose monohydrate. Water was added through a nozzle assembly as shown in FIG. 9, the nozzle having an effective area of 0.480 mm$^2$, at various flow rates between 110 g/min and 240 g/min, and at temperatures from 32° C. to 42° C. The container systems were filled to contain approximately 90 ml of solution. All the solids had dissolved by the time 90 g of the water had been provided into the container system.

Example 6

The solution formed in Example 3 was withdrawn from the container system through the nozzle assembly at flow rates up to 50 ml/min, based on the needs of a dialysis system. The solution formed in Example 4 was withdrawn from the container system through the nozzle assembly at flow rates of 0.875 ml/min or 1.17 ml/min. The solution formed in Example 5 was withdrawn from the container system through the nozzle assembly at decreasing flow rates, as indicated in the Table 1.

TABLE 1

| Example Step Procedure for Container Effluence | | |
| --- | --- | --- |
| Infusion Step | Flow Rate (mL/min) | Step Duration (min) |
| 1 | 46 | 1 |
| 2 | 23 | 1 |
| 3 | 11 | 1 |
| 4 | 6 | 1 |
| 5 | 3 | 1 |
| 6 | 1 | 1 |

Though 46 ml/min was the highest flow rate used based on operational needs, there was no indication this was a practical limit for flow through the nozzle assembly.

Additional non limiting example embodiments of the disclosure are described below.

Embodiment 1

A container system comprising at least one flexible wall defining a compartment containing a dissolvable solid or concentrate, a support adjacent a first end of the at least one flexible wall, and a nozzle assembly coupled to a second end of the at least one flexible wall. The second end of the wall is distal from the first end. The nozzle assembly comprises a hollow body defining a longitudinal axis. The hollow body further defines a plurality of orifices through a wall thereof. Each orifice is able to form a fluid connection between an interior volume within the hollow body and the compartment. Each orifice is configured to deliver liquid from the interior volume to the compartment in a direction having an angle of between 5° and 85° from a direction of the longitudinal axis.

Embodiment 2

The container system of Embodiment 1, further comprising a frangible seal configured to limit transfer of material from the compartment through the nozzle assembly until the frangible seal has been breached.

Embodiment 3

The container system of Embodiment 2, wherein the frangible seal comprises an adhesive bonded to the at least one flexible wall within the compartment.

Embodiment 4

The container system of any one of Embodiments 1 through 3, further comprising a port configured to couple a fluid conduit to the nozzle assembly.

Embodiment 5

The container system of any one of Embodiments 1 through 4, wherein only a single fluid conduit connects the compartment to an exterior of the container system at any one time.

Embodiment 6

The container system of any one of Embodiments 1 through 5, wherein the nozzle assembly is configured to receive a solution from the compartment and deliver the solution to a conduit external to the compartment.

Embodiment 7

The container system of any one of Embodiments 1 through 6, wherein the at least one flexible wall defines at least one seam adjacent the nozzle assembly at the second end of the at least one flexible wall, and wherein at least one orifice of the plurality is configured to deliver liquid from the interior volume to the compartment in a direction substantially parallel to the at least one seam.

Embodiment 8

The container system of Embodiment 7, wherein the at least one seam comprises a horizontal bottom seam, and wherein at least one orifice of the plurality is configured to deliver liquid substantially horizontally from the interior volume to the compartment.

Embodiment 9

The container system of any one of Embodiments 1 through 8, wherein the nozzle assembly extends into the compartment a distance between about 1 mm and about 10 mm.

Embodiment 10

A nozzle assembly comprising a hollow body having a generally cylindrical exterior surface and defining a longitudinal axis, and a port configured to couple to a catheter. The hollow body defines a plurality of orifices therethrough. Each orifice is able to form a fluid connection between an interior volume within the hollow body and an exterior volume outside the nozzle assembly. Each orifice is configured to deliver liquid received from the port to the exterior volume in a direction forming an angle of between 5° and 85° with respect to a direction of the longitudinal axis of the hollow body.

Embodiment 11

The nozzle assembly of Embodiment 10, wherein at least one orifice of the plurality is wherein the angle is at least 10°.

Embodiment 12

The nozzle assembly of Embodiment 11, wherein the angle is at least 20°.

Embodiment 13

The nozzle assembly of any one of Embodiments 10 through 12, wherein at least one orifice of the plurality is oriented such that liquid flowing through the at least one orifice leaves the nozzle assembly traveling in a direction at an angle of at least 5° with respect to a direction normal to an exterior surface of the nozzle assembly.

Embodiment 14

The nozzle assembly of Embodiment 13, wherein the at least one orifice of the plurality is oriented such that liquid flowing through the at least one orifice leaves the nozzle assembly traveling in a direction at an initial angle of at least 10° with respect to a direction normal to an exterior surface of the nozzle assembly.

Embodiment 15

A method for delivering a liquid, comprising providing a plurality of streams of a liquid through a nozzle assembly into a compartment containing a dissolvable solid or concentrate, mixing the dissolvable solid or concentrate with the liquid to form a solution, and withdrawing the solution after mixing from the compartment through the nozzle assembly. The compartment is defined by at least one flexible wall having a support adjacent a first end of the at least one flexible wall. The nozzle assembly is coupled to a second end of the at least one flexible wall distal from the first end, the nozzle assembly comprising a hollow body defining a longitudinal axis. The hollow body defines a plurality of orifices therethrough, each orifice able to form a fluid connection between an interior volume within the hollow body and the compartment. Each orifice is configured to deliver the liquid from the interior volume to the compartment in a direction having an angle of between 5° and 85° from a direction of the longitudinal axis.

Embodiment 16

The method according to Embodiment 15, wherein providing a plurality of streams of a liquid through a nozzle assembly into a compartment comprises forming a rotational flow of the liquid in the compartment.

Embodiment 17

The method according to Embodiment 15 or Embodiment 16, further comprising breaching a frangible seal before providing the plurality of streams of the liquid through the nozzle assembly into the compartment.

Embodiment 18

The method according to any one of Embodiments 15 through 17, wherein withdrawing the solution from the compartment through the nozzle assembly comprises varying a flow rate of the solution through the nozzle assembly.

Embodiment 19

The method according to Embodiment 18, wherein varying a flow rate of the solution through the nozzle assembly comprises decreasing the flow rate in a stepwise manner.

Embodiment 20

The method according to any one of Embodiments 15 through 19, wherein withdrawing the solution from the compartment through the nozzle assembly begins less than five minutes after providing a plurality of streams of a liquid through a nozzle assembly begins.

While the description has been presented herein with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors. Further, embodiments of the disclosure have utility with different and various container types and configurations.

What is claimed is:

1. A container system comprising:
   at least one flexible wall defining a compartment containing a dissolvable solid or concentrate;
   a support adjacent a first end of the at least one flexible wall; and
   a nozzle assembly coupled to a second end of the at least one flexible wall, the second end distal from the first end, the nozzle assembly comprising a hollow body defining a longitudinal axis;
   wherein the hollow body further defines a plurality of orifices through a wall thereof, the plurality of orifices recessed into an outer surface of the nozzle assembly, one or more of the plurality of orifices oriented at an angle of between 5° and 85° relative to the longitudinal axis, each orifice able to form a fluid connection between an interior volume within the hollow body and the compartment, the one or more of the plurality of orifices defined by a first hole in an inner surface of the hollow body proximate the interior volume and a second hole in an outer surface of the hollow body proximate the compartment, wherein the first hole has a first cross-sectional shape and the second hole has a second different cross-sectional shape larger than the first cross-sectional shape and each orifice configured to deliver liquid from the interior volume to the compartment in a direction having an angle of between 5° and 85° from a direction of the longitudinal axis.

2. The container system of claim 1, further comprising a frangible seal configured to limit transfer of material from the compartment through the nozzle assembly until the frangible seal has been breached.

3. The container system of claim 2, wherein the frangible seal comprises an adhesive bonded to the at least one flexible wall within the compartment.

4. The container system of claim 1, further comprising a port configured to couple a fluid conduit to the nozzle assembly.

5. The container system of claim 1, wherein only a single fluid conduit connects the compartment to an exterior of the container system at any one time.

6. The container system of claim 1, wherein the nozzle assembly is configured to receive a solution from the compartment and deliver the solution to a conduit external to the compartment.

7. The container system of claim 1, wherein the at least one flexible wall defines at least one seam adjacent the nozzle assembly at the second end of the at least one flexible wall, and wherein at least one orifice of the plurality is configured to deliver liquid from the interior volume to the compartment in a direction substantially parallel to the at least one seam.

8. The container system of claim 7, wherein the at least one seam comprises a horizontal bottom seam, and wherein at least one orifice of the plurality is oriented in a substantially horizontal orientation.

9. The container system of claim 1, wherein the nozzle assembly extends into the compartment a distance between about 1 mm and about 10 mm.

10. A container system comprising:
    at least one flexible wall defining a compartment containing a dissolvable solid or concentrate;
    a support adjacent a first end of the at least one flexible wall; and
    a nozzle assembly coupled to a second end of the at least one flexible wall, the second end distal from the first end, the nozzle assembly comprising a hollow body defining a longitudinal axis;
    wherein the hollow body further defines a plurality of orifices through a wall thereof, the plurality of orifices recessed into an outer surface of the nozzle assembly, one or more of the plurality of orifices oriented at an angle of between 5° and 85° relative to the longitudinal axis, each orifice able to form a fluid connection between an interior volume within the hollow body and the compartment, the one or more of the plurality of orifices defined by a first hole in an inner surface of the hollow body proximate the interior volume and a second hole in an outer surface of the hollow body proximate the compartment, wherein the first hole has a first cross-sectional shape and the second hole has a second cross-sectional shape different from the first cross-sectional shape and each orifice configured to deliver liquid from the interior volume to the compartment in a direction having an angle of between 5° and 85° from a direction of the longitudinal axis.

11. The container system of claim 10, wherein the second cross-sectional shape of the second hole is larger than the first cross-sectional shape of the first hole.

* * * * *